United States Patent [19]

Dukes et al.

[11] Patent Number: 5,016,642

[45] Date of Patent: May 21, 1991

[54] SLOW MOTION CARDIAC IMAGING

[75] Inventors: John N. Dukes; Paul Lum, both of Los Altos; John D. Larson, Palo Alto, all of Calif.

[73] Assignee: Hewlett-Packard Company, Palo Alto, Calif.

[21] Appl. No.: 508,377

[22] Filed: Apr. 11, 1990

[51] Int. Cl.$^5$ .............................................. A61B 5/04
[52] U.S. Cl. ............................... 128/696; 128/660.07; 128/710
[58] Field of Search ............. 128/660.07, 695, 653 R, 128/696, 710

[56] References Cited

U.S. PATENT DOCUMENTS

| | | | |
|---|---|---|---|
| 3,734,086 | 5/1973 | Phelps, Sr. | 128/2.06 R |
| 4,027,663 | 6/1977 | Fischler et al. | 128/2.06 R |
| 4,263,548 | 4/1981 | Carlson et al. | 324/102 |
| 4,271,437 | 6/1981 | Scott | 360/9 |
| 4,346,403 | 8/1982 | Tamura | 358/93 |
| 4,346,718 | 8/1982 | Morris | 128/710 |
| 4,364,397 | 12/1982 | Citron et al. | 128/710 |
| 4,382,184 | 5/1983 | Wernikoff | 128/653 R |
| 4,513,753 | 4/1985 | Tabata et al. | 128/706 |
| 4,593,314 | 6/1986 | Siler | 128/660.07 |
| 4,710,717 | 12/1987 | Pelc et al. | 324/309 |
| 4,821,731 | 4/1989 | Martinelli et al. | 128/653 R |
| 4,881,549 | 11/1989 | Rhyne | 128/660.07 |
| 4,936,311 | 6/1990 | Oe | 128/695 |

OTHER PUBLICATIONS

Havlice and Taenzer, "Medical Ultrasonic Imaging: An Overview of Principles and Instrumentation", Proc. I.E.E.E., vol. 67, 1979, pp. 620–641.
Hewlett Packard Journal, Oct. 1983, pp. 3–40.

Primary Examiner—Francis Jaworski
Assistant Examiner—George Manuel

[57] ABSTRACT

Apparatus and method for representing slow motion of an oscillating heart by forming strobed images of the heart at a sequence of uniformly spaced times with controllable time interval lengths that are related to, but not identical to, the primary oscillation period T of the heart. The heart images may be formed at a sequence of times $t = t_0 + kMT_h/N$ where $t_0$ is an initial time, N is a positive integer, $k = 1, 2, \ldots, N-1$ and M is a positive integer. Alternatively, the heart images may be formed at a sequence of times determined in part by the current oscillation cycle of the heart.

14 Claims, 2 Drawing Sheets

SLOW MOTION CARDIAC IMAGING

TECHNICAL FIELD

This invention relates to slow motion display of heart images derived from real time heart images produced by acoustic imaging apparatus and the like.

BACKGROUND OF THE INVENTION

It is often desirable to display a stop action or slow motion view of a heart over one or several oscillation cycles of the heart. This can be done using a cine loop that records real time acoustical imaging signals, either digitally or on magnetic tape. The images are then played back slowly in sequence to simulate slow motion of the heart. The cine loop apparatus is usually complex and expensive and must repeat the recorded cycle in order to simulate continuous slow motion.

Apparatus for measuring and displaying the time lapse between the time of a heart beat, recorded electrocardiographically, and a corresponding pulse produced at a periphery of a limb of the body, is disclosed by Phelps in U.S. Pat. No. 3,734,086. The apparatus measures pulse propagation time from the heart to an extremity of the body and uses the same operational position in the heart cycle for each time lapse measurement. Images of the heart at different positions in the heart cycle are not formed.

Apparatus for measuring the time interval between two consecutive heartbeats and for counting the number of such time intervals that are of substantially equal length is disclosed in U.S. Pat. No. 4,027,663, issued to Fischler et al., in U.S. Pat. No. 4,346,718, issued to Morris, in U.S. Pat. No. 4,364,397, issued to Citron et al., and in U.S. Pat. No. 4,513,753, issued to Tabata et al. These patents do not disclose formation of an image of the heart at different positions in the heart cycle. The Citron et al. patent also monitors the length of the period of the heart primary oscillation cycle to determine whether this period indicates that a regular rhythm is present.

Scott, in U.S. Pat. No. 4,271,437, discloses a time lapse videotape editor and controller that permits formation of images of a scene at a desired frequency for a predetermined time interval.

In U.S. Pat. No. 4,263,548 issued to Carlson et al., apparatus is disclosed that accepts or measures a first time interval of length $\Delta t$, then immediately generates a second time interval of length $\Delta t/n$ where n is apparently an integer. At the end of this second time interval a strobe pulse is generated that may be used to turn on certain analog voltage, current or resistance measuring circuits. The patent does not disclose or suggest how, if at all, the apparatus might be used to time repetitive measurements on cyclic phenomena.

Animated illustration, using photographs of a plurality of drawings showing an object in motion at a sequence of times that are spaced apart by a small time interval to give the appearance of smooth motion, is disclosed by Tamura in U.S. Pat. No. 4,346,403. The photographs are stored in an image storage device and are redisplayed individually to permit an artist to produce "in-between" drawings that show the moving object(s) at intermediate times that do not coincide with the image formation times.

In U.S. Pat. No. 4,710,717, Pelc et al. disclose a method for fast scan cinematographic imaging of a heart cycle using nuclear magnetic resonance ("NMR") imaging techniques. This method contemplates formation of more than one image during a heart cycle because the NMR process requires considerable time to form images. Thus, the technique probably does not extend to formation of images of a heart over an arbitrary number of oscillation cycles of the heart.

What is needed here is a technique that is inexpensive and relatively simple to apply and that allows formation of a sequence of images of the heart at different positions throughout a heart oscillation cycle, where the image formation period may extend over as many oscillation cycles as desired and may be displayed in real time.

SUMMARY OF THE INVENTION

These needs are met by a method of cardiac imaging that divides the electrical signal representing a primary oscillation cycle of the heart into N time intervals, each of approximately equal length $\Delta t$, so that a time interval of length $N\Delta t$ approximately coincides with and includes at least one oscillation cycle, where N is a positive integer. Thus, an image of the heart at a sequence of times $t_k = t_0 + kM\Delta t$ is formed, where $t_0$ is a predetermined initial time, $k = 0, 1, 2, \ldots$, and M is another predetermined positive integer. For example, with the choices $N = 8$ and $M = 5$, images of the heart would be formed at a sequence of times $t_0$, $t_0 + (5/8)T_h$, $t_0 + (10/8)T_h$, $t_0 + (15/8)T_h$, etc., at time intervals of length approximately $5/8$ of a fundamental period of the heart. Images of the heart are formed at a sequence of times similar to "strobing" in order to form a sequence of images at time intervals that are approximately uniformly spaced. For example, if the images are formed at a sequence of times separated by time intervals $(N+1)\Delta t$, each successive image will be advanced in time by $(1 + 1/N)$ cycles of the heart relative to the immediately preceding image, and a sequence of N such images will present a cycle of the heart extending over a time period of $N+1$ successive oscillation cycles of the heart. If, instead, the images of the heart are formed at a sequence of times separated $(N-1)\Delta t$, this will correspond to retardation rather than advancement in time and will present a cycle of images of the heart extending over a time interval of length equal to $N-1$ oscillation cycles of the heart.

Apparatus suitable for forming a sequence of images at times $t_k = t_0 + kM\Delta t$ in one embodiment may include a phase locked loop including a phase comparator and a voltage controlled oscillator ("VCO"). A first input signal to the phase comparator may be an oscillatory signal with a frequency equal to the heart cycle or fundamental oscillation rate. A second input signal to the phase comparator may be an oscillatory signal whose frequency is equal to the VCO output signal divided by N. The frequency output signal from the VCO, divided by $M = (N+m)$, (m and M integers, $M \geq 1$, $m \geq -(N-1)$) is also fed to frame control means that freezes the display of a moving heart produced by an imaging system, until the next such signal arrives. In such an imaging system, images are generally formed and displayed at a frequency much higher than the heart rate so that, if the display is periodically frozen in this way, the heart appears to move in slow motion.

BEST MODE FOR CARRYING OUT THE INVENTION

Figure 1:
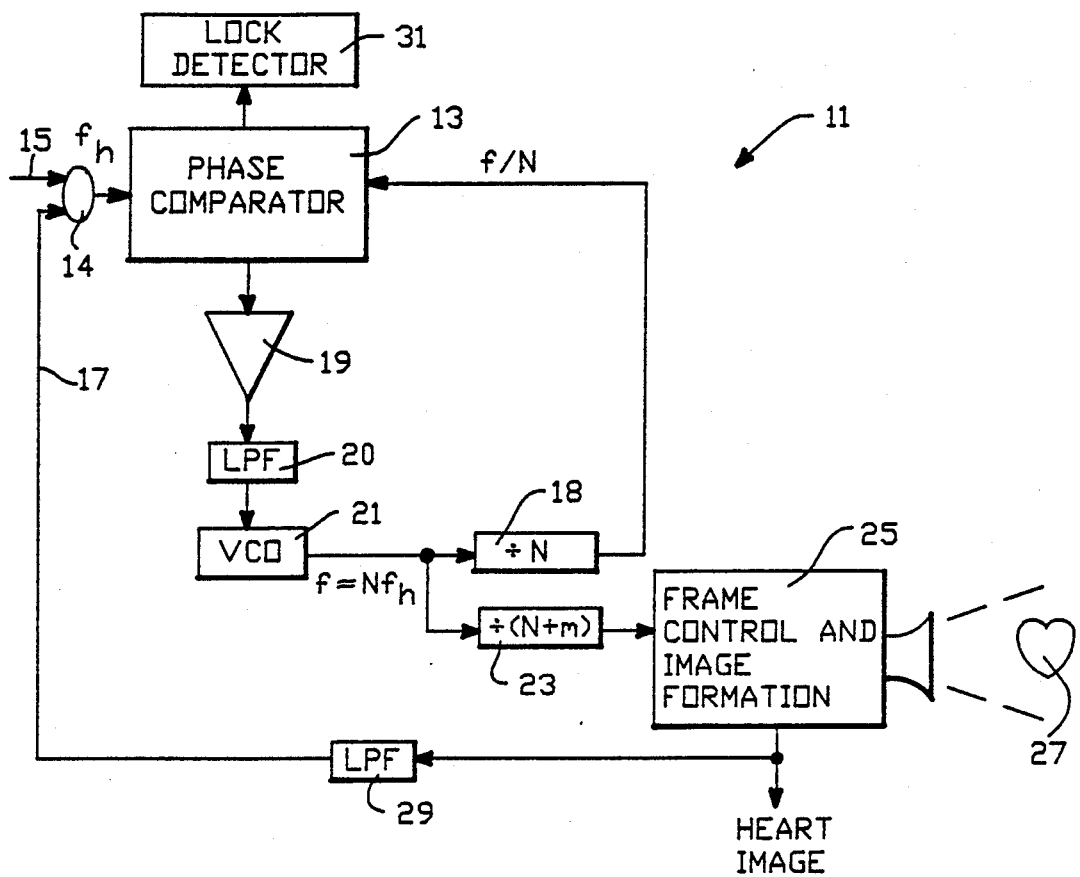
FIG. 1 is a plan view of an embodiment of the invention for formation of images of the heart at a sequence of uniformly spaced times.

With reference to FIG. 1, one embodiment 11 of apparatus for practicing the invention includes a phase comparator 13 having two input terminals and an output terminal. A first input terminal of the comparator 13 receives an oscillatory electrical signal, whose frequency is approximately the frequency of the heart fundamental oscillation rate $f_h$, from a first frequency source. This signal may be provided by an external sensor (not shown), such as electrocardiograph electrodes attached to the heart, on a first input line 15, by suitably-processed video imaging of the heart on a second (alternative) input line 17, or by some other suitable process. A switch or multiplexer 14 determines whether the signal on the signal line 15 or on the signal line 17 shall be passed to the comparator 13. Acoustical imaging of body organs is discussed, for example, in the Hewlett Packard Journal, October 1983, pp. 3-40 and by Havlice and Taenzer, "Medical Ultrasonic Imaging: An Overview of Principles and Instrumentation," *Proc.* I.E.E.E., vol. 67, 1979, pp. 620-641.

The fundamental heart oscillation rate $f_h$ is the inverse of the period $T_h$ of a complete cycle of the heart. A second input terminal of the comparator 13 receives the output signal from a first frequency divider circuit 18, whose input signal will be described later. The phase comparator 13 receives the two oscillatory input signals and issues an output signal whose voltage amplitude increases or decreases monotonically with increase of the phase difference between the two input signals. The output signal from the phase comparator 13 is received by an amplifier 19 (optional), and the output signal from the amplifier is received by a low pass filter (LPF) 20 (optional). The output signal from the LPF 20 is received by a voltage controlled oscillator 21 whose output signal is an oscillatory signal with a frequency f that increases (or decreases) monotonically with increase of the voltage received at the input terminal of the VCO. The oscillatory output signal from the VCO 21 is received by the input terminal of the first frequency divider circuit 18 that divides the frequency f by N, and is also received by a second frequency divider circuit 23 that divides f by M=N+m, where M is a positive integer (m ≧ -(N-1)).

The phase comparator 13 will respond to the first and second input signals received thereat by attempting to drive the VCO 21 so that the output signal from the comparator 13 is as close to zero as possible. This comparator output signal will be zero or have a small stationary value only if the frequency f/N of the oscillatory signal output from the VCO 21 and the fundamental heart oscillatory frequency $f_h$ satisfy the relation $$f/N - f_h = 0 \quad (1)$$

or $f = Nf_h$. The output signal frequency from the VCO 21 is also divided by an integer N+m in the second frequency divider circuit 23 to produce a time-varying signal of frequency $Nf_h/(N+m)$ (m an integer ≧ -(N-1)). This signal drives a frame control within a typical acoustic imaging system 25 that freezes displays of periodic images of the heart 27. Choice of the integer m determines the length of the time interval between any two consecutive images of the heart (equal to $MT_h/N$, where M is a positive integer). A close analogy to this technique is use of a light strobe to observe the blades of a fan advancing slowly, stopping or retreating slowly over a time interval of about several complete cycles of rotation of the fan blades.

The cardiac synchronization signal of frequency $f_h$ that is provided on input line 17 may be extracted from a video signal produced by the image formation means 25 from the heart 27 and passed through a low pass filter 29 (optional) to the signal line 17, also illustrated by FIG. 1.

Figure 2:
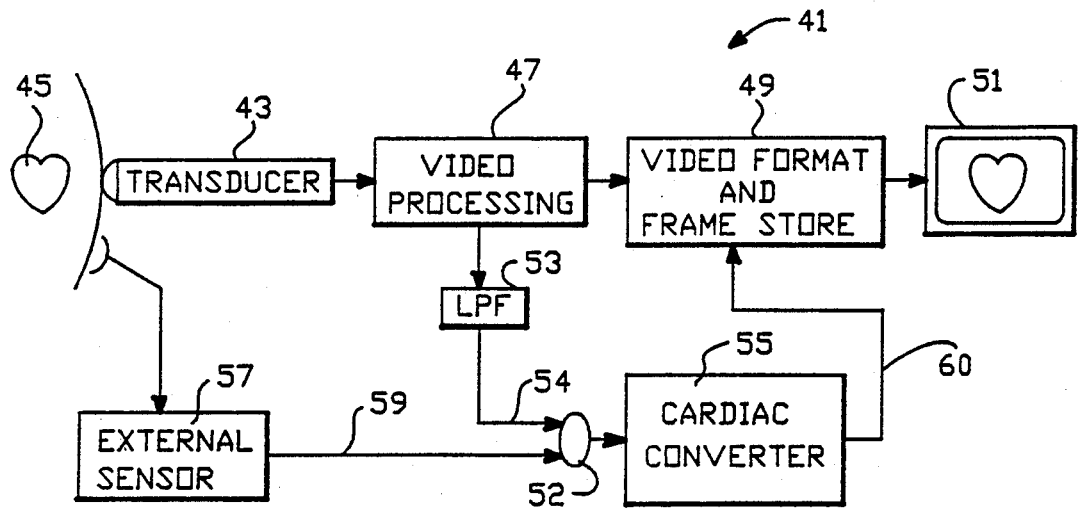
FIG. 2 is a plan view of the environment for frame control and image formation means used in the invention.

FIG. 2 illustrates an environment in which the invention might operate. A transducer or other similar device 43 receives an acoustical image signal from the heart 45 and converts this signal to an electrical signal that is received by a video processing module 47. The module 47 provides a complex electrical signal, typically referred to as "video", which can be modified further or directly used to drive a display. But if such a signal is low pass filtered by a low pass filter 53 to remove all higher frequencies, the signal can furnish a filtered signal on a line 54 at the heart oscillation frequency $f_h$. A low pass cutoff frequency of the order of 5 Hz may be provided for this purpose.

The video processing module 47 also forms a sequence of video signals and passes these to a video format and frame store module 49. Normally, the frame store module 49 receives a sequence of video image signals in rapid succession from the video processing module 47, which are then passed onto a CRT or other display module 51. However, in order to provide a slow motion cardiac image, only a subset of this sequence of images is stored by the frame store module 49 and displayed. A heart image is stored by the frame store module 49 and displayed only when this module receives a pulse from the frequency divider circuit 23 in FIG. 1; that is, at time intervals of length approximately equal to $(1+m/N)T_h$. All other image signals received by the frame store module 49 from the video processing module 47 may be disposed of without being stored (or displayed) so that the memory requirements of the frame store module 47 are modest; that is, only one frame need be stored while it is being displayed. An external heart sync signal, provided on a signal input line 59 by an external sensor 57, and an internal heart sync signal, provided on the signal input line 54 by the video processing module 47, are passed to a switch 52 that chooses one of these signals and passes it to a slow motion cardiac converter 55 that controls image formation times.

The output of the cardiac converter 55 is passed to the frame store module 49 on a signal line 60. The external heart sync signal issued by the external sensor 57 is passed along the signal input line 59 to the switch 52.

Returning to FIG. 1, a portion of the video output signal from the image formation means 25 in FIG. 1 is received by a second low pass filter 29 whose cutoff frequency $f_c$ is set somewhat above the heart's expected maximum cycle rate, for example $f_c = 5$ Hz. The output signal from the cutoff filter 29 should contain only the fundamental heart cycle signal itself, and this output signal can provide the signal of frequency $f_h$ on the second input line 17 that is received by the phase comparator 13. Only one of the two signals received on the input lines 15 and 17 should be delivered to the comparator 13, and the choice is made by the switch 14 adjacent to the comparator. Optionally, a lock detector 31 can be provided to receive a lock/no-lock signal from the comparator 13 to sense when phase lock (satisfaction of Eq. (1)) has been achieved.

Figure 3:
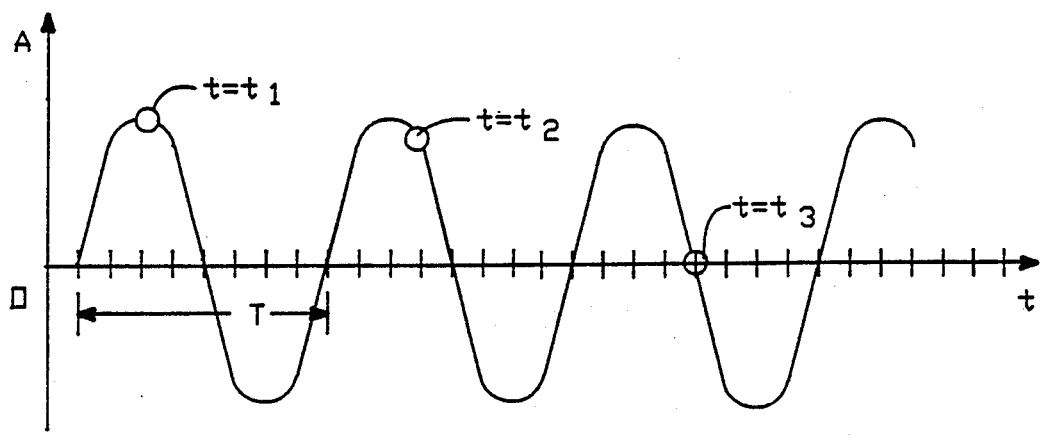
FIG. 3 is a graphical view of several primary oscillation cycles of the heart, illustrating a suitable sequence of times for which an image thereof can be formed according to the invention.

FIG. 3 illustrates three fundamental oscillation cycles of the heart, having fundamental oscillation period $T_h$, and a sequence of time points $$t_k = t_0 + k\left(1 + \frac{m}{N}\right)T_h \; (m \geq -(N-1))$$

at which images of the heart might be formed with the choices $m=1$, $N=8$ and $k=0,1,2$. With this choice, images of the heart would be formed at eight uniformly spaced time points over nine fundamental oscillation cycles of the heart. This choice corresponds to advancement within the cycles. The choice of time points $$t_k = t_0 - k\left(1 + \frac{m}{N}\right)T_h \; (-(N-1) \leq m \leq N-1)$$

for imaging corresponds to retardation within the cycles, and the choice $t_k = t_0 + kT_h$ corresponds to "frozen" motion in which the heart image is formed at approximately the same position in each cycle.

Figure 4:
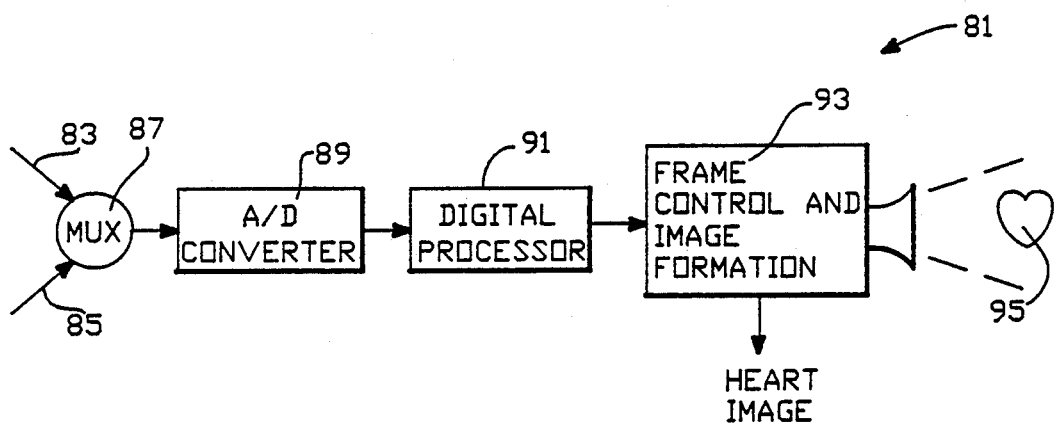
FIG. 4 is a plan view of a digital embodiment of the invention.

Another class of embodiments 81, shown in FIG. 4, uses digital, rather than analog, processing to control the rate at which heart image frames are stored and displayed. An internal heart sync signal and an external sync signal are provided on a first and second input lines 83 and 85, respectively, to an operator-controlled switch or multiplexer 87 that determines which of these two signals is used to determine image formation rate. The chosen heart sync signal, with associated period $T_h = 1/f_h$, is accepted at the switch 87 and is passed through an A/D converter 89 (optional) to a digital processor 91. In one embodiment the digital processor 91 may include a digital version of the analog phase locked loop shown in FIG. 1, with separate operator-controlled input switches to specify the positive integers m and N that occur in determination of the sequence of image formation times $t_k = t_0 + k(m/N)T_h$ ($k=0, 1, 2, \ldots$), or alternatively the frequency $f = (m/N)(1/T_h)$, at which heart images are selected and presented. The digital processor 91 serves at least two purposes: (1) to provide an estimate $T_h$ of the present heart oscillation cycle; and (2) to use the choices of positive integers m and N to cause the frame control and image formation means 93 to form and store a sequence of heart images at time $t_k = t_0 + k(m/N)T_h$ ($k=0, 1, 2, \ldots$). The digital processor 91 then communicates with the frame control and image formation means 93 that forms and stores the sequence of images of the heart 95.

The digital processing module 91 may include a sample-and-hold circuit to sample and store the measured values of $T_h$, denoted $T_{-n}$ ($n=1, 2, 3, \ldots, p$), for the p heart oscillation cycles that immediately precede the present heart cycle, whose actual measured value $T_h$ is not yet known. The current estimated value of fundamental heart period to be used is then determined as a moving average $$T_h = \sum_{n=1}^{p} w_n T_{-n} \tag{2}$$

The $w_n$ are real weight numbers, which may be positive, negative or zero, satisfying the relation $$\sum_{n=1}^{p} w_n = 1 \tag{3}$$

The weight numbers $w_n$ and the length p of the averaging interval may be chosen by the operator. For example, if the immediately preceding value $T_{-1}$ is used as a "best guess" of the current value of heart sync period $T_h$ the operator would choose $w_{-1}=1$ and $w_{-n}=0 (n \geq 2)$. The actual value of $T_h$ is also determined by measurement and is added to the string of measured values $T_{-n}$ ($n=1, 2, \ldots, p$) to allow determination of the next estimate or moving average $T_h$.

Figure 5:
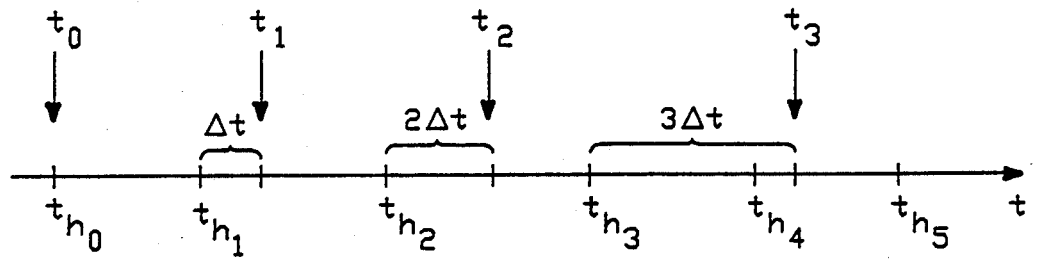
FIG. 5 illustrates a sequence of heart beats and a sequence of heart image formation and display times according to an embodiment of the invention.

FIG. 5 illustrates another technique for generating the slow motion heart image formation timing. First select a fixed time increment $\Delta t$ that is much less than an average heart period, for example $\Delta t = 100$ nsec. After each heart rate synch signal is received, at times $t = t_h$ ($k=1, 2, 3, \ldots$), a multiple $k\Delta t$ of the fixed time increment is added and a new heart image is formed at each of the freeze frame times $t_k$ defined by $$t = t_k = t_{hk} + k(\Delta t) \; (k=0, 1, 2, \ldots)$$

Initially, each freeze frame interval defined by $t_k \leq t < t_{k+1}$ ($k=1, 2, 3, \ldots$) will contain one heart synch signal time $t = t_{hk}$ at which a heart signal is received. However, the length of these freeze frame intervals increases without limit. At some point in time two or more heart synch signals will be received within the same freeze frame interval $t_k \leq t < t_{k+1}$. This is illustrated in FIG. 5, where the first freeze frame interval in which two (or more) heart synch signals are received is the interval $t_2 \leq t < t_3$, during which the two heart synch signals at times $t = t_{h3}$ and $t = t_{h4}$ are received. At the end of this first such interval, namely at $t = t_3$, the heart image formation timing is reset to zero, and the process illustrated in FIG. 5 is repeated.

As an example, assume the heart synch signal has a frequency of 1 Hz and is unchanging and that the time increment chosen is $\Delta t = 150$ nsec. The freeze frame times are then defined by $$t = t_k + 1 = t_{hk} + k\Delta t = t_0 + k(1.15 \text{ sec}).$$

For the k values $k=0, 1, 2, 3, 4,$ and 5, precisely one heart synch signal will occur in the freeze frame interval $t_k \leq t < t_{k+1}$. However, during the freeze frame interval $t_5 \leq t < t_6$, two heart synch signals will occur, namely those at the times $t = t_6$ and $t = t_7$. At the time t=t₇, then, the times would be reset and a new sequence of heart images would be formed according to the above procedure.

The time increment Δt may also be defined adaptively, based upon a current moving average of the length of a heart oscillation cycle or on other changing estimates, but this time increment should preferably be fixed for formation of a consecutive sequence of heart images as illustrated in FIG. 5.

In addition to the phase locked loop technique, the moving average technique, the polynomial predictor technique and the fixed time increment/variable length technique, many other techniques may be used in the digital processor 91 in FIG. 4. However, these examples suffice to illustrate the variety of techniques available to determine the times for formation, storage and display of images of the heart.

We claim:

1. A method for representing slow motions of an oscillating heart, the method comprising the steps of:
   providing an oscillatory electrical signal of frequency $f_h$ representing an estimate of the oscillation cycle of the heart; and
   using the signal of frequency $f_h$, providing a sequence of electrical image signals of the heart at a frequency $f=(1+m/N)f_h$, where N is a predetermined positive integer and m is an integer satisfying $-(N-1) \leq m < N$, so that each of this sequence of electrical signals occurs in a different oscillation cycle of the heart.

2. The method of claim 1, wherein said step of providing an oscillatory electrical signal representing an oscillation cycle of said heart comprises the steps of:
   passing said electrical image signals of said heart through a low pass filter that substantially suppresses all oscillatory signals except the fundamental oscillation cycle of said heart; and
   providing the output signal of the low pass filter.

3. The method of claim 1, wherein said step of providing said estimate $f_h$ of said oscillation cycle frequency of said heart comprises the steps of:
   providing measured lengths of p preceding heart oscillation measuring cycles, denoted $T_{-n}$ (n=1, 2, ..., p), and storing frequencies $f_{-n}=1/T_{-n}$ (n=1, 2, ..., p), where p is a predetermined positive integer;
   providing a sequence of weight numbers $w_n$ (n=1, 2, ..., p) that are real and satisfy the relation $$\sum_{n=1}^{p} w_n = 1; \text{ and}$$

providing said estimate $f_h$ as a sum $$(f_h)^{-1} = \sum_{n=1}^{p} w_n (f_{-n})^{-1}.$$

4. The method of claim 3, the step of providing said weight numbers $w_n$ further comprises providing a moving average for said estimate $f_n$.

5. A method for forming slow motion images of an oscillating heart that produces a heart image synchronization signal representing completion of a heart oscillation cycle at a sequence of consecutive times $t_{h0} < t_{h-1} < t_{h2} < \ldots$, the method comprising the steps of:
   determining a positive time increment Δt that is much less than an average heart cycle length;
   monitoring the actual heart oscillation cycle and determining the end, at times $t=t_{hk}$ (k=0, 1, 2, ...), of each of a sequence of consecutive heart oscillation cycles;
   using the times Δt and $t_{hk}$ to form and display a sequence of heart images at a sequence of image formation times given by $$t=t_k=t_{hk}+k(\Delta t) \text{ (k=0, 1, 2, \ldots, K)}$$

where the time interval defined by $t_K > t < t_{K+1}$ is the first such time interval for which two or more heart oscillation cycles end within that time interval.

6. Apparatus for representing slow motions of an oscillating heart, the apparatus comprising:
   a source of an oscillatory digital signal of frequency $f_{in}$ approximately equal to the fundamental oscillation frequency of the heart;
   a digital processor having an input terminal to receive the oscillatory digital signal of frequency $f_{in}$ and to produce and issue an oscillatory output signal of frequency $f_{out}=f_{in}/(1+m/N)$, where N is a positive integer and m is an integer satisfying $-(N-1) \leq m$;
   image formation means for receiving the digital processor output signal as an input signal thereto and, at the completion of each oscillation cycle of the image formation means input signal, for forming and issuing an image of the heart as an output signal after completion of an oscillation cycle,
   whereby each image formation means output signal is formed during a different oscillation cycle of the heart.

7. Apparatus for representing slow motions of an oscillating heart, the apparatus comprising:
   a phase comparator having first and second input terminals to receive first and second signals and to form a difference signal proportional to a difference of these two signals, and having a comparator output terminal to issue the difference signal as an output signal;
   a source for providing an oscillatory signal of frequency $f_h$ approximately equal to the fundamental oscillation frequency of the heart, with this oscillatory signal being received at the first input terminal of the phase comparator;
   a voltage controlled oscillator having an input terminal to receive the output signal from the phase comparator and having an oscillator output terminal to issue as an output oscillatory signal whose oscillation frequency f varies monotonically with the voltage amplitude of the output signal from the phase comparator;
   a first frequency divider circuit, having an input terminal to receive the oscillatory signal of frequency f from the voltage controlled oscillator and having a first divider circuit terminal, to form and issue an oscillatory output signal at the first divider circuit output terminal with a frequency equal to f/N, where N is a predetermined positive integer, with this output signal being received by the second input terminal of the phase comparator;
   a second frequency divider circuit, having an input terminal to receive the oscillatory signal of frequency f from the voltage controlled oscillatory and having a second divider circuit terminal, to form and issue an oscillatory output signal at the second divider circuit terminal with a frequency equal to $f/(N+m)$, where m is an integer satisfying $-(N-1) \leq m$; and image formation means for receiving the oscillatory output signal from the second frequency divider circuit as an input signal at an image formation means input terminal and, after completion of each oscillation cycle of the input signal, for forming and issuing a sequence of images of the heart as an output signal, with each heart image being formed in a different oscillation cycle of the heart.

8. The apparatus of claim 7, further comprising a low pass filter, having a cutoff frequency that is above but approximately equal to the frequency of the primary oscillation cycle of the heart, which receives said image formation means output signal and issues an output signal that serves as said oscillatory input signal for said first frequency divider circuit.

9. The apparatus of claim 7, wherein said oscillatory signal source comprises external sensor means for forming and issuing an oscillatory output electrical signal representing a heart oscillation cycle of said frequency $f_h$.

10. The apparatus of claim 7, wherein said image formation means comprises:

transducer means for receiving an input signal representing an image of the heart and for forming and issuing an output electrical signal that represents the input signal;

video processing means for receiving the transducer means output signal as an input signal and for forming and issuing an output electrical signal that provides a sequence of video signals representing images of the heart; and video frame means, having first and second input terminals, for receiving the sequence of video signals from the video processing means at the first input terminal, for receiving said second frequency divider circuit output signal at the second input terminal, and for forming and displaying an image of the heart for each oscillatory cycle of the signal received at the second input terminal.

11. The apparatus of claim 10, wherein said image formation means further comprises an output terminal for issuing an oscillatory output electrical signal from said transducer means or from said video processing means that represents a fundamental oscillation cycle of the heart, and this output terminal serves as said source of said oscillatory signal of said frequency $f_n$.

12. The apparatus of claim 11, further comprising a low pass frequency filter, positioned to receive an input signal from said image formation means output terminal and to issue an output signal that is received by said first input terminal of said phase comparator, the filter having a low pass cutoff frequency that is higher than but approximately equal to a representative value of said fundamental oscillation frequency of the heart.

13. The apparatus of claim 10, wherein said oscillatory signal source comprises:

external sensor means for forming and issuing an oscillatory output electrical signal representing a heart oscillation cycle of said frequency $f_h$;

an output terminal on said image formation means for issuing an oscillatory output electrical signal from said transducer means or from said video processing means that represents a fundamental oscillation cycle of the heart; and a switch having first and second input terminals to receive the external sensor means output signal and the output signal from said image formation means, respectively, and having an output terminal connected to said first input terminal of said comparator, that issues one of the first and second switch input signals as an oscillatory output signal of said frequency $f_h$.

14. Apparatus according to claim 13, wherein said oscillatory signal source further comprises a low pass frequency filter, positioned to receive an input signal from said image formation means output terminal and to issue an output signal that is received by said first input signal terminal of said phase comparator, the filter having a low pass cutoff frequency that is higher than but approximately equal to a representative value of said fundamental oscillation frequency of the heart.

* * * * *